(12) United States Patent
Faget-Mora

(10) Patent No.: US 11,957,711 B2
(45) Date of Patent: Apr. 16, 2024

(54) FOGONAZO SOLUTION

(71) Applicant: Reinaldo Faget-Mora, Bonita Springs, FL (US)

(72) Inventor: Reinaldo Faget-Mora, Bonita Springs, FL (US)

(73) Assignee: Reinaldo Foget Mora, Bonita Springs, FL (US)

( * ) Notice: Subject to any disclaimer, the term of this patent is extended or adjusted under 35 U.S.C. 154(b) by 207 days.

(21) Appl. No.: 17/187,753

(22) Filed: Feb. 27, 2021

(65) Prior Publication Data

US 2022/0273704 A1  Sep. 1, 2022

(51) Int. Cl.
*A61K 33/20* (2006.01)
(52) U.S. Cl.
CPC .................................. *A61K 33/20* (2013.01)

(58) Field of Classification Search
None
See application file for complete search history.

(56) References Cited

U.S. PATENT DOCUMENTS

| 8,784,900 B2 * | 7/2014 | Northey | A61K 33/20 |
| | | | 252/181.7 |
| 2020/0281969 A1 * | 9/2020 | Burd | A61K 9/08 |

OTHER PUBLICATIONS

Dolina et al.( Anesteziologiya i Reanimatologiya, (1997) vol. 0, No. 3, pp. 52-56). Dolina et al. teach, Seventy-five patients with severe pneumonia were treated with sodium hypochlorite solution (intravenous drip in concentration 600 mg/liter) (Year: 1997).*

\* cited by examiner

*Primary Examiner* — Alton N Pryor

(57) ABSTRACT

Rapid, corrective treatment for respiratory tract infections; using a safe ultra-low dose of a derivative of chlorine.

5 Claims, 1 Drawing Sheet

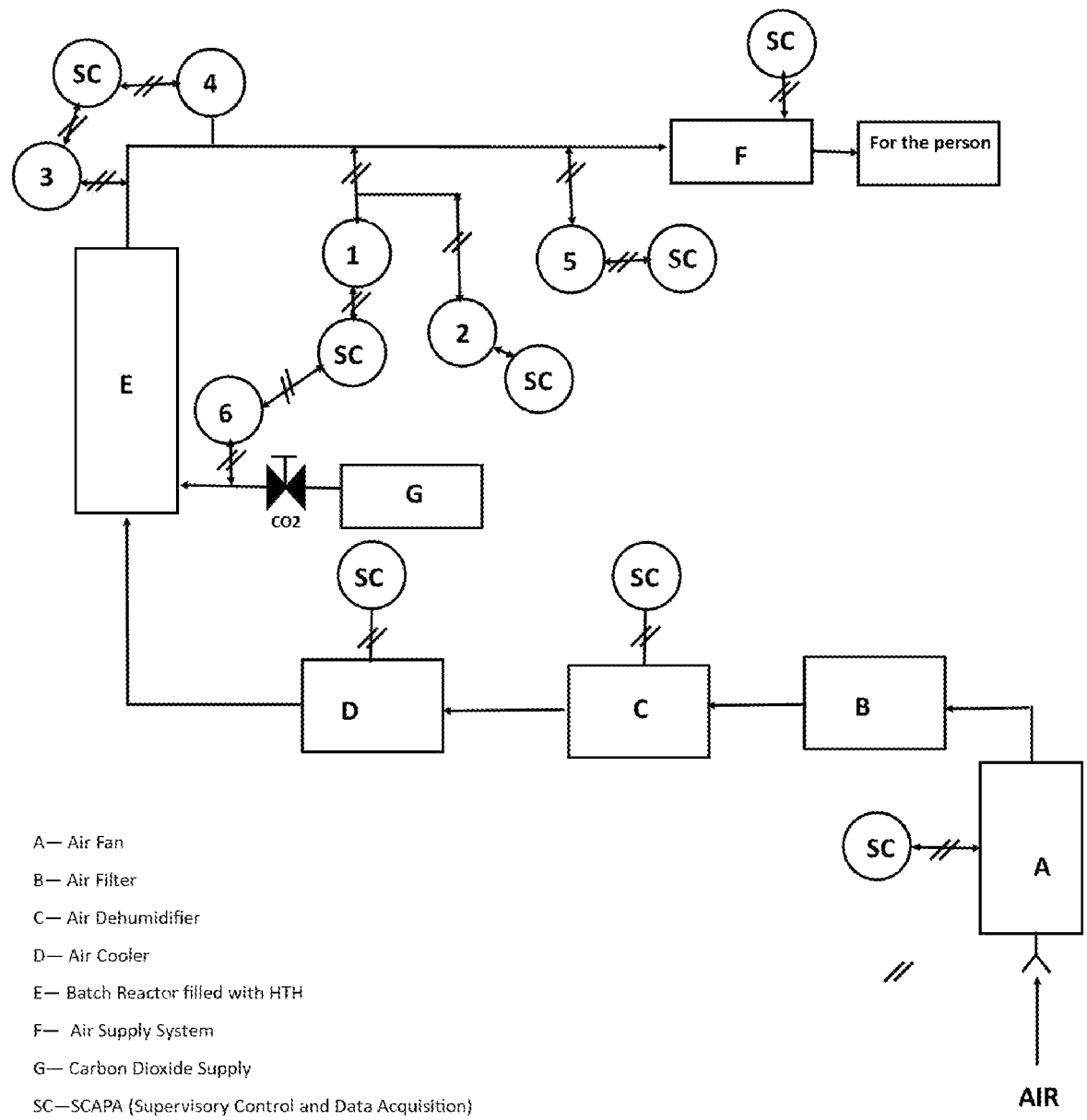
A— Air Fan
B— Air Filter
C— Air Dehumidifier
D— Air Cooler
E— Batch Reactor filled with HTH
F— Air Supply System
G— Carbon Dioxide Supply
SC—SCAPA (Supervisory Control and Data Acquisition)
1— Chlorine Gas Analyzer
2— Dichlorine Dioxide Analyzer
3— Pressure Gauge
4— Thermometer for Gas Mixture
5— Flow Meter for Gas Mixture
6— Flow Meter for Carbon Dioxide

FOGONAZO SOLUTION

BACKGROUND OF THE INVENTION

I. Description of the Prior Art

It is known that many diseases occur in the respiratory tract, both in the upper and lower. This is caused by viruses, bacteria, and fungi.

The following are examples of diseases in the respiratory tracts:

Upper respiratory infections (nose, nasal, paranasal sinuses cavity, pharynx)
  Common cold
  Tonsillitis
  Laryngitis
Lower respiratory tract infections (larynx, trachea, primary bronchi, bronchioles, and alveoli)
  Pneumonia
  Bronchitis
  Tuberculosis
Disease related to respiratory tract infection a such:
Severe acute respiratory syndrome (SARS-COV2)
Middle east respiratory syndrome (MERS)

It is of top priory that the United States develops a safe and effective way to disinfect the respiratory tract. Any problem must have a solution that meets the following conditions:
  The solution must be selective about the cause of the problem.
  It must be totally safe to avoid side effects.
  The solution must be easy to apply. It must be able to be administered in any location and at any time.
  It should have a minimal cost for an application.

II. Field of the Invention

Disinfection using a chemical compound.

For an effective disinfection of the respiratory system, 1) chlorine derivative must be used that has the greatest disinfection to kill germs at a low dose, 2) cause minimal damage to the entire respiratory system, which means selective action on pathogenic microorganisms be transported in the gas phase to the lungs with minimal decomposition of the chemical, 3) a rapid mass transfer of the disinfectant from the gas phase to the liquid phase, 4) minimum time to kill germs, 5) It is very important that the disinfectant is compatible with the natural process already occurring in body. The disinfection process will be sustainable from the nose to the pulmonary alveoli.

Fundamental concept of the disinfection process.

Hypochlorous acid (HCLO), is the chemical compound that produces the best disinfection. It is produced by the human immune system through cells called neutrophils (white blood cells) that kill invasive organism. It disinfects 200 to 300 times better than bleach and is 100% safe.

Hypochlorous acid—disinfection mode

Hypochlorous acid is a weak acid formula (HCLO) and is a strong disinfection agent. It also reacts with a wide variety of biomolecules such as DNA, RNA, fatty acids groups, cholesterol, and proteins. The effects of this reagent are powerful on germs, inhibitions of glucose oxidation, depletion of adenine, nucleotides, inhibition of DNA replication, protein unfolding and aggregation.

Hypochlorous acid is generated in activated neutrophils by myeloperoxidase—mediated peroxidation of chlorine ions.

During a respiratory burst, neutrophils produces H2O2 which converts to HCLO by the activity of granule enzyme myeloperoxidase in the following reaction.

% O2+H2O→H2O2 (NaDPh oxidase enzyme)

H2O2+CL−+H+→HCLO+H2O (M PO enzyme)

HC1O→Kill pathogen

HCLO properties and uses
Chemical formula—HClO
Molar mass—52.46 g/mol
Appearance—odorless aques solution
Density—variable
Acidity (Pka)—7.53
Conjugate base—Hypochlorite
Boiling point—125-130 C
Self-Decomposition when it is pure.
Powerful oxidizing agent
Used as disinfecting agent in drinking and wastewater treatment.

The next question is—how to transport hypochlorous acid into the respiratory system effectively?

The transport of the reagent must be done in the gaseous phase of breathed air.

Currently, it is impossible to transport hypochlorous acid in the gas phase; but there is another way to do this.

What is the other way to do it?

A chemical able to be transformed into hypochlorous acid and can be transported into the gas phase as:

Dichlorine monoxide, formula=CL2O

When combined with liquid water it produces hypochlorous acid quickly and spontaneously according to the following reaction:

CL2O+H2O→2HCLO

In the inhalation stage, air is taken into the lungs. When exhalation occurs, liquid water molecules remain in the respiratory tract. When dichlorine monoxide is introduced into the inhalation stage liquid water and CL2O reacts. The water in the form of an aerosol provides a very large reaction surface for the chemical reaction to occur efficiently. The conversion of CLO2 to HCLO will be practically 100% in a short period of time.

The other question is: how to reach the lethal concentrations of hypochlorous acid on the walls of the respiratory tract with the mass of the gas CL2O being low? In this disinfection process, the respiratory tract works like a chemical reactor, reacting in the gas phase, but HCLO is transferred to the liquid phase in a microlayer. The minimum amount of hypochlorous acid formed dissolves into a very thin layer of water. Mathematically speaking, the concentration is very high because the volume of the water is very low.

In summary: a microlayer of the hypochlorous acid solution is formed on the walls of the respiratory tract. It is microscopic and very specific to destroy germs very selectively without destroying the body's cells.

Characteristics and properties of CLO2
Name—Di-chlorine Monoxide
Other names—Oxygen dichlorine
Dichlorine oxide
Chlorine Oxide
Hypochlorous Oxide
Hypochlorous Acid Anhydride
Properties:
Chemical formula—CLO2

Molar mass—86.9054 g/mol
Appearance—reddish brown liquid
Yellowish brown gas
Boiling point—2.0 C or 2.2 C
Liquid density—3.552 g/L
Solubility in water—very soluble 143 g/100 g
Heat of vaporization 26.3 KH/mol
Solubility in other solvent—soluble in CCL4
Melting point—120.6 C
Standard enthalpy of formation +80.3 KJ/mol
Photochemistry—photodissociation eventually forming O2 and CL2

(2CLO→CL2+O2)

Explosive properties—it is explosive at concentration above 23.5% in the gas phase minimum explosive limit with electric spark.
Temperatures above 120 C can produce explosive conditions.
Liquid di-chlorine has been reported to be shock sensitive.
Chemical reaction with water:

CL2O+H2O→2HCLO

The equilibrium of the reaction is shifted to the formation of the hypochlorous acid.
It is incompatible with:
Carbon, di-cyanogen, diphenylmercury, nitrogen oxide, oxidizable materials, potassium, alcohols, ammonia, antimony sulfide, arsenic, barium sulfide, calcium phosphide, charcoal, corks, ethers, hydrogen sulfide, mercury sulfide, paper, phosphine, phosphorus, rubber, sulfur, any oxidizable materials as methane, propane, ethylene Uses—Dichlorine monoxide has been used as an intermediate in the manufacture of calcium hypochlorine and in the manufacturing of calcium hypochlorite and the sterilization for outer-space applications. Its uses are for the preparation of chlorinated solvents and chloroisocyanurates has been described. Dichlorine monoxide has been effective in bleaching pulp and textiles. It also can be used as etchant in semiconductor manufacturing. It is also a good chlorinating agent.

Materials to handle CL2O
PVC, CPVC, Viton, Teflon—best use Teflon
Do not use with Polypropylene, carbon steel, stainless steel, neoprene.
Safety measures for handling dichlorine monoxide gas
Must be procedures standardized by state and federal legislation.
We can cite general measures such as storage, handling, dosage, gas concentration to supply, temperature and pressure to keep the operation safe.

Storage—light opaque Teflon must be used.
Handling—avoid any contact with oxidizable products that are on the list of materials for handling; the time between the synthesis of the product (CL2O) and its use must be the minimum; Teflon material in the connections where the gas flows.

Gas concentration/composition—control of gas (CL2O) composition in storage as well as supply is vital, relatively low concentration of the gas in 23.5% could generate self-explosion, a maximum 5% must be maintained to be in a safe work area; the gas must be mixed with filtered dry air with a moisture content of 7-12 C dew point. The composition of the gas-air mixture that will be supplied to be breathed will be calculated. In reference to chlorine gas. As a fundamental concept is the dosage of the mixed gas is to maintain the value of the NOAEL (no-observed-adverse-effect-level) that is a toxicological concept when a harmful product is in haled, this value is internationally recognized for chlorine gas=0.5 ppm (parts per million); valve for dichlorine monoxide:

CL2O→CL2+½O2

CL2O Molar Mass=87 g/mol (CL2O)

CL2 Molar Mass=71 87/71=1.23.2021

1.23×0.5=0.61 ppm of CL2O—this is the maximum value that must be maintained to dose the product; this means that an average per sum can be inhaling this gas mixture for 8 hours without adverse effects, in 24 hours the value would be:

(0.61×8)/24=0.20 ppm

As a fundamental principle ultralow doses will be preserved. Values in mg/liters for gaseous mixtures for 8 hours:

Mg/liters=(ppm×molas mass)/24200=(0.61×86.9054)/24200=0.0028 ppm

Summary Toxicology Table:

| Number | Item | Value | Units |
|---|---|---|---|
| 1 | NOAEL | 0.0022 | Mg/Liters in 8 hours |

NOAEL = Non observed adverse effect level

Gas concentration sensors will be recording and signaling. Visual and audible alarms will be available. The detection system must be checked before any operation to guarantee a safe process.

Temperature—the primary gas obtained must be kept between 15 to 25 degrees centigrade. Never heat the mixture! Temperature control through the process is essential.

Pressure—atmospheric pressure is what will govern the process. Avoid overpressure. Regularly observe the pressure gauges.

What is the technology behind the process?

Technologies for synthesizing dichlorine monoxide are widely known across the spectrum of process engineering, but a form of production that is relatively easy to apply must be sought. Avoid contamination with heavy metals, anything toxic or any pollutants.

Ways to synthesis dichlorine monoxide gas:

1) Treat mercury oxide II with chlorine gas, however this method is expensive as well as highly dangerous due to the high risk of mercury poisoning.

2CL2+HgO→HgCL2+CL2O

2) Chemical reactions between chlorine and sodium carbonate

2CL2+Na2HCO3+H2O→CL2O+2NaHCO3+2NaCL

2CL2+2NaHCO3→CL2O+2NaCL+2CO2+H2O

In the absence of water. This requires heating to 150-250 C as dichlorine monoxide is unstable at the temperatures. It must therefore be continuously removed to prevent thermal decomposition.

2CL2+Na2CO3→CL2O+CO2+2NaCL.

3) There is another way to obtain the correct concentrations of dichlorine monoxide gas. This method is the easiest and less complicated. This method allows us to reach values lower than 0.0022 mg/Liter.

Dichlorine monoxide gas is generated by using HTH (High Test Hypochlorite)

This method was used in the early 1945 by researchers William J Elford and Mr. Joan Van Den Ende at the "National Institute for Medical Research, London, N.W. 3". The results of their research were successful, and they obtained concentrations of monoxide dichlorine gas around 1.25 ppm (parts per million in gas) which is the maximum allowable concentration. They used HTH and carbon dioxide. The experiments compared the disinfection effect in a room between an aerosol of sodium hypochlorite solution and the gas dichlorine monoxide.

Concept of the chemical reaction of the process.

The following chemical reaction occurs in a heterogeneous phase between HTH (solid) and carbon dioxide (gas).

$$Ca(CLO)2\ (solid)+CO2\ (gas)\rightarrow CaCO3\ (Solid)+CL2O\ (gas)$$

HTH in pellet form reacts with carbon dioxide gas in a stoichiometric way where carbon dioxide is the limiting substance in the chemical reaction. Carbon dioxide is injected together with previously filtered and dehumidified air at atmospheric pressure and temperature between 15-25 C. The gas mixture must remain in this temperature range. The process flow must be designed to obtain concentrations of the dichlorine monoxide gas around 0.0022 mg/Liter maximum with an inhalation time of 8 hours maximum. Collaterally, chlorine gas could be generated which would be undesirable. This is solved with the following measures:

1) Use HTH that is new.
2) Pass filtered and tempered dry air prior to gas generation and remove traces of chlorine.
3) Install sensors for chlorine gas and dichlorine monoxide gas to monitor the concentration of these gases in the gas mixture.
4) Create the mixture of CLO2 5 to 10 minutes maximum before use to avoid the decomposition of the gas.

General Notes on the procedure:

1. Use minimal amounts of HTH for one time use. Remember that calcium carbonate is formed in the chemical reaction and resists the interaction of carbon dioxide. Few grams of the HTH are expected to be used in the reaction.
2. Experimental tests to establish the concentration of carbon dioxide in the mixture, granulometry of HTH, reaction time, volume of HTH, solid/gas volume ratio, and mixing of gaseous streams. The gas supply time for inhalation is very important which for safety will not exceed 5 hours, this time is expected to be shortened to a few minutes.
3. The form of gas generation will be by standardized batch not continuous.

Process flow sheet: See Flow Sheet Process Page

There are three ways to supply gas. See Verses Time Graph on separate page.

I. Pulse input
II. Step input
III. Mixed input

Estimation of the residence time of the gas supplied to the respiratory tract. In the respiratory cycle of the adults (average) at resting conditions. The respiratory minute volume we can calculate the amount of air moved each minute multiplying the respiratory rate=12 breaths/minute. Tidal volume=500 ml/breath Volume of air moved each minute=12×500=6000 ml/minute Total lung capacity is 6000 ml in males. 4200 ml in females Residence time for males—(6000×2)/6000=2 minutes Residence time for females—(4200×2)/6000=1.4 minutes This means that the contact time of the reagent will be about 2 minutes in males and 1.4 minutes in females (70% less than males). These times are propitious to reach better results in the disinfection reaction because the hypochlorous acid kills the germs in a few seconds.

BRIEF DESCRIPTION OF THE DRAWING

The forgoing and other features of the present invention will become more fully understood. This represents a schematic view of the overall system for generating dichlorine monoxide gas.

SUMMARY OF THE INVENTION

This procedure is designed as a method of corrective treatment in the respiratory tract infections using a chlorinated derivative compound—dichlorine monoxide (CL2O) in the gas phase at ultra low doses withing the range that does not harm the body.

The chlorinated gas reacts chemically with the aerosol water particles found in the respiratory tract, producing hypochlorous acid molecules that condense on the wall of the respiratory tract into a film that is friendly to cells of the respiratory tract. The hypochlorous acid that is formed is a highly powerful, fast acting disinfectant and does not destroy the cells of the respiratory tract so having low concentrations of the compound is an achievable disinfectant action that is also efficient. This method is a complementary action to the work of the neutrophilic cells of the body defense system which also produces hypochlorous acid to eliminate invading dangerous germs. CL2O gas doses that do not exceed the concentration of 0.0022 mg/Liter must be carefully administered as a breathing treatment within a maximum time of 8 hours.

Constant monitoring of flow, composition, temperature, and the pressure of the gaseous stream will be in strict compliance with instruments of the highest quality and low error range. CL2O gas can be obtained on site or supplied in small bottles with all safety measures. It is recommended to generate the gas using HTH. Also, do not use any toxic products such as mercury.

What is claimed is:

1. A method of treating a respiratory tract infection comprising administering to a person in need thereof a gaseous composition consisting essentially of dichlorine monoxide to treat the respiratory tract infection, wherein the dichlorine monoxide is the only active ingredient in the composition.

2. The method of claim 1 wherein the respiratory tract infection being treated is pneumonia.

3. The method of claim 1 or 2 wherein a maximum concentration of 0.0022 mg/L dichlorine monoxide is administered.

4. A method of treating a respiratory tract infection comprising administering to a person in need thereof a gaseous composition comprising 0.0022 mg/L dichlorine monoxide, wherein hypochlorous acid and hypochlorous acid anhydride are not present in the composition and wherein the dichlorine monoxide is the only active ingredient in the composition.

5. The method of claim 4 wherein the respiratory tract infection being treated is pneumonia.

\* \* \* \* \*